United States Patent [19]

Kreeger

[11] 4,319,067
[45] Mar. 9, 1982

[54] METHOD FOR INCREASING THE ACTIVITY OF FRIEDEL-CRAFTS CATALYST

[75] Inventor: Russell L. Kreeger, Somerville, N.J.

[73] Assignee: Union Carbide Corporation, New York, N.Y.

[21] Appl. No.: 174,028

[22] Filed: Jul. 31, 1980

[51] Int. Cl.³ .............................. C07C 2/70; C07C 5/22
[52] U.S. Cl. ....................................... 585/459; 585/474
[58] Field of Search .................................. 585/459, 474

[56] References Cited

U.S. PATENT DOCUMENTS

| | | | |
|---|---|---|---|
| 3,031,513 | 4/1962 | Earhart et al. | 585/459 |
| 3,427,254 | 2/1969 | Muller et al. | 252/415 |
| 3,819,735 | 6/1974 | Argento | 585/474 |
| 3,846,334 | 11/1974 | De Fiore et al. | 585/459 |
| 3,848,012 | 4/1974 | Applegath et al. | 585/459 |
| 3,927,134 | 12/1975 | Yanagihara et al. | 585/459 |

*Primary Examiner*—Curtis R. Davis
*Attorney, Agent, or Firm*—Francis M. Fazio

[57] ABSTRACT

The catalyst activity in the Friedel-Crafts alkylation of aromatic compounds or the transalkylation of monoalkyl or polyalkyl aromatic compounds is increased by the addition of gaseous hydrogen halide directly to the catalyzed alkylation or transalkylation reaction mixture.

11 Claims, No Drawings

METHOD FOR INCREASING THE ACTIVITY OF FRIEDEL-CRAFTS CATALYST

BACKGROUND OF THE INVENTION

Aromatic compounds such as isopropylbenzene, ethylbenzene, butylbenzene and similar compounds have found wide use in many applications and particularly in the production of monomers used in aromatic polymers. Two of the major methods of producing aromatic compounds such as these are the Friedel-Crafts alkylation reaction of aromatic compounds with alkyl halides, alkenes or alkynes and the Friedel-Crafts transalkylation reaction of monoalkyl or polyalkyl aromatic compounds with aromatic compounds. Frequently in industrial practice both of these reactions occur in the same process. The aromatic compound is alkylated to produce mixtures of the monoalkyl aromatic and polyalkyl aromatic compounds. The alkylated aromatics produced during the reaction are transalkylated with unsubstituted aromatic compound to produce additional quantities of desired monosubstituted aromatic compound.

These alkylation and transalkylation reactions are generally catalyzed by a metal halide-based Friedel-Crafts catalyst system which is typically composed of a metal halide containing a hydrogen halide or alkyl halide cocatalyst. The catalyst mixture can be employed in either the solid or liquid phase; the liquid phase is often preferred industrially because it is generally easier to inject into the reactor and easier to regulate. When the liquid phase is employed, a catalyst complex composed of metal halide catalyst, hydrogen halide or alkyl halide cocatalyst, and monoalkyl aromatic and/or polyalkyl aromatic compounds is used. Although this catalyst complex can be formed in situ, it is preferred that the catalyst complex be generated separately and subsequently introduced to the reaction mixture. This is preferable because the catalyst complex can be prepared at a lower temperature than the reaction temperature and thus have a higher activity due to the substantial avoidance, at the lower temperature, of side reactions that lead to compounds that may poison a portion of the catalyst.

As the alkylation or transalkylation reaction proceeds, the catalyst is gradually deactivated and must be regenerated. In the past, regeneration has generally been accomplished by separation of catalyst from the reaction and treatment with regenerative compounds, such as hydrogen chloride, hydrogen, aluminum, aluminum chloride, and some aliphatic hydrocarbons. This separation and subsequent regeneration is costly and time consuming. A further problem encountered is the lessened catalyst activity, resulting in reduced yield, due to the employment of the partially deactivated catalyst. A method of regenerating the catalyst complex which will require less cost than heretofore possible and will improve the catalyst activity would be highly desirable.

SUMMARY OF THE INVENTION

It has now been found that the addition directly to the Friedel-Crafts-catalyzed alkylation or transalkylation reaction of a gaseous hydrogen halide, such as hydrogen chloride, will reactivate, in situ, the catalyst complex and will result in significant increases in catalyst activity. The catalyst activity is increased because the catalyst is operating at near maximum activity throughout the reaction rather than in successive stages of gradual deactivation as has been heretofore the case. Another advantage of the process of this invention is reduced costs due to the avoidance of costly external regeneration procedures and also because smaller amounts of catalyst need be initially employed due to the increases in catalyst activity. A further advantage is increased reaction selectivity to desired product by a reduction in side reactions due to the smaller amounts of catalyst that can now be feasibly employed. Another advantage is a reduction in pollution achieved by the capability of regenerating catalyst which is in too small an amount to economically justify regeneration by heretofore known methods; these deactivated catalysts have been merely discharged as effluent.

DESCRIPTION OF THE INVENTION

This invention is an improved method for producing alkaryls by the Friedel-Crafts alkylation or transalkylation reactions. The improvement comprises supplying gaseous hydrogen halide to the catalyzed reaction mixture, while the reaction is proceeding. This improvement surprisingly and unexpectedly increases the activity of the catalyst and decreases the amount of catalyst required resulting in improved catalyst selectivity to desired product.

The Friedel-Crafts alkylation reaction in which the process of this invention is useful is the reaction of aromatic hydrocarbons, unsubstituted or substituted with such substituents as halide, alkyl having from 1 to 20 carbon atoms, alkoxy having from 1 to 20 carbon atoms and the like, and, illustrative of which one can name benzene, toluene, xylene and many others well known to those skilled in the art, with alkyl halide having from 1 to 20 carbon atoms such as methyl chloride, dichloromethane, isopropyl chloride, ethyl bromide, ethyl iodide, ethyl fluoride, lauryl chloride and the like, or with alkenes, substituted or unsubstituted, having from 2 to 20 carbon atoms such as ethylene, propylene, isobutylene, 1,11-dodecadiene, eicosene, and the like, or with alkynes, substituted or unsubstituted having from 2 to 20 carbon atoms sush as acetylene, propylene, 2-butyne and the like, to form monoalkaryls or polyalkaryls such as ethylbenzene, isopropylbenzene, diethylbenzene, diisopropylbenzene and the like.

The Friedel-Crafts transalkylation reaction in which the improvement of this invention is useful is the reaction of a monoalkyl or polyalkyl aromatic compound having from 7 to about 100 carbon atoms, preferably from 7 to 40 carbon atoms such as toluene, xylene, diisopropylbenzene, 1,3,5-triethylbenzene, didodecylbenzene, ethyl toluene, and the like, with aromatic hydrocarbon as described above for the alkylation reaction, to form the monoalkaryls or polyalkaryls described above for the alkylation reaction.

Often, especially in industrial application, the alkylation and transalkylation reactions occur concurrently; for example, when the alkylation reaction forms mixtures of monoalkyl aromatic and polyalkyl aromatic compounds, undesired polyalkyl aromatic may then be transalkylated with unreacted monosubstituted aromatic reactant initially charged to form more desired aromatic compound. Illustrative of such a situation is the alkylation of benzene with propylene to form desired isopropylbenzene and undesired diisopropylbenzene. The diisopropylbenzene then reacts with benzene in a transalkylation reaction to form more desired isopropylbenzene.

Both the alkylation and transalkylation reactions are catalyzed by the same catalyst system which is composed of a metal halide catalyst and a hydrogen halide or alkyl halide cocatalyst. Metal halides suitable for use in the catalyst system are the Lewis acids and include aluminum chloride, ferric chloride, aluminum bromide, boron trifluoride, stannic chloride, zinc chloride, antimony pentachloride, titanium tetrachloride, and others known to those skilled in the art. Suitable hydrogen halide cocatalysts include hydrogen chloride, hydrogen fluoride, hydrogen bromide, and the like. Suitable alkyl halides are those having from 1 to 20 carbon atoms such as methyl chloride, ethyl chloride, isopropyl chloride, ethyl bromide, butyl fluoride, eicosyl chloride and the like. When an alkyl halide is employed as cocatalyst, the alkyl group should be similar to that of the alkylating agent used in the alkylation; for example, if one employs propylene in the alkylation, one should employ a three carbon halide, such as isopropyl chloride, as cocatalyst if one desires to use an alkyl halide as cocatalyst.

The reactive catalyst complex can be produced in situ or separately, as is known in the art. When produced in situ the desired quantities of metal catalyst and hydrogen halide or alkyl halide cocatalyst are added directly to the reactor. When produced separately the metal halide and hydrogen halide or alkyl halide are initially mixed in a separate reactor with a portion of the aromatic compound to react to form a liquid complex. Typically this is accomplished by mixing metal halide with aromatic solvent followed by addition of hydrogen halide or alkyl halide. This mixture then undergoes agitation until the metal halide dissolves; if the hydrogen halide or alkyl halide cocatalyst employed is gaseous, the addition of the cocatalyst is done in such a manner so that this gaseous cocatalyst essentially saturates the liquid mixture. The liquid complex is then added to the reactor as needed. This procedure is often done commercially because of ease of handling and regulating the catalyst mixture. When the catalyst complex is prepared separately from the reaction mixture, the aromatic solvent employed is generally one of the aromatic reactants that is to be alkylated or transalkylated; there can also be present other solvents which do not interfere substantially with the catalytic activity of the reaction.

The composition of the catalyst complex, based on one mole of metal halide, comprises from 0.1 to 10 moles, preferably from 0.5 to 1.5 moles of hydrogen halide or alkyl halide and from 0.5 to 10 moles, preferably from 0.5 to 2 moles of solvent. The catalyst complex is used in any catalytically effective amount preferably from about 0.01 to about 5 weight percent of metal halide based on the weight of the aromatic compounds present in the reaction mixture.

The alkylation of transalkylation reaction is carried out at a temperature of from 20° C. to 150° C., preferably from 65° C. to 115° C., most preferably from 80° C. to 105° C.

The reaction pressure can be subatmospheric, atmospheric or superatmospheric; often it is convenient to carry out the reaction at reflux.

The time of the reaction will vary and will depend on such factors as the temperature, pressure, catalyst concentration and batch size as well as the specific reactants and catalyst system employed.

In the improved process of this invention, as the reaction is carried out, gaseous hydrogen halide is added to the reactor to substantially maintain the maximum catalyst activity. The hydrogen halide can be the same as the hydrogen halide cocatalyst, if one is employed, or it may be different; the preferred hydrogen halide is hydrogen chloride. As the gaseous hydrogen halide is introduced to the reactor, it is desirable that the gas be dispersed to as great a degree as possible to facilitate contact between the gas and the catalyst. One convenient way to accomplish this is to sparge the gaseous hydrogen halide into the reactor; of course, as is well known, the pressure of the hydrogen halide must exceed that which is inside the reactor so that the gas will enter the reactor. It is often convenient to introduce the gaseous hydrogen halide to the reactor at a constant rate although this is not essential to the practice of this invention.

The gaseous hydrogen halide is introduced to the reactor in a concentration of at least 0.01 mole per mole of metal halide, preferably from 0.01 to 20 moles per mole of metal halide, most preferably from 0.1 to 1 mole per mole of metal halide. In a batch process, gaseous hydrogen halide is added during the reaction such that a total of from 0.01 to 20 moles of hydrogen halide are added per mole of metal halide over the time of the reaction. In a continuous process gaseous hydrogen halide is added during the reaction such that a total of 0.01 to 20 moles of hydrogen halide are added per mole of metal halide being added per unit time. The upper limits enumerated above are merely for illustrative purposes; there is no strict upper limit for the amount of hydrogen halide added to the reaction to generate the catalyst.

In a typical laboratory scale embodiment, the reactants are charged to a reaction flask along with liquid catalyst complex, heated to the desired temperature and the gaseous hydrogen is introduced to the reaction continuously at the desired concentration and pressure, until the reaction is terminated. It is well-known that commercially these Friedel-Crafts alkylation and transalkylation processes are generally run continuously.

The improved method of this invention results in less catalyst usage per unit of desired product produced. This has significant economic advantages both because less catalyst is needed and also because costly and time consuming post reaction catalyst regeneration techniques which had heretofore been necessary can now be avoided. A further advantage is the increased selectivity which one may now obtain due to the reduction in the amount of catalyst required. A particularly useful application of the improved method of this invention is in those processes where the concentration of catalyst is too low to justify reactivation. Such processes are those which employ a catalyst concentration of about 1 weight percent or less of metal halide based on the weight of the aromatic compounds in the reaction mixture. Heretofore, in such processes, the catalyst was simply hydrolyzed when the reaction was completed and as such presented a waste disposal problem. Now, by the use of the improved method of this invention, even those catalysts used in low concentrations can be reactivated.

There have been many techniques used by those skilled in the art to reactivate Friedel-Crafts alkylation or transalkylation catalysts; but all of the known techniques required separation of the catalyst from the reaction mixture before reactivation. Now by use of the improved process of this invention, Friedel-Crafts alkylation or transalkylation catalysts can be reactivated in situ; thus less catalyst is consumed, yield of desired product is increased and the cost of catalyst reactivation is significantly reduced.

The following examples serve to further illustrate the invention. They are not intended to limit the invention in any way.

EXAMPLE 1

There was charged to a 1000 ml, 4-neck reaction flask equipped with a paddle stirrer, septum, gas inlet tube, and Claisen adapter with thermometer and condenser, a mixture of 32 grams of diisopropylbenzene in 456 grams benzene. The mixture was dehydrated by azeotropic distillation of 100 ml (88 grams) benzene and water and the reaction flask purged with nitrogen.

A catalyst complex was prepared by reacting 2.67 grams of aluminum chloride with 5.84 grams of diisopropylbenzene, 1.31 grams of benzene and 1.79 grams of isopropyl chloride at ambient temperature for one hour, maintaining atmospheric pressure by releasing excess generated hydrogen chloride. This resulted in the formation of two layers, a top layer of excess solvent and a bottom layer of catalyst complex. Separation was effected by syringing out the catalyst layer.

The catalyst complex was added to the reaction flask in an amount such that the aluminum chloride was 0.105 weight percent based on the weight of the diisopropylbenzene-benzene mixture. The temperature of the reaction mixture was raised to reflux approximately 82°–83° C., at one atmosphere, and gaseous anhydrous hydrogen chloride was added continuously to the reaction at a constant rate in such a manner that in 60 minutes 15 molar equivalents per mole of aluminum chloride were added to the reaction mixture. After 60 minutes, gas chromatographic analysis showed an 86 percent transalkylation of diisopropylbenzene to the desired isopropylbenzene.

For comparative purposes the above-described procedure was repeated except that the gaseous hydrogen chloride was not added during the reaction. After 60 minutes, gas chromatographic analysis showed a diisopropylbenzene transalkylation to isopropylbenzene of only 47 percent.

The results demonstrate that the improved process of this invention greatly increases the catalyst activity; in this case the increase in diisopropylbenzene transalkylation was from 47 percent to 86 percent, signifying a catalyst activity increase of 83 percent.

EXAMPLE 2

In a manner similar to that described in Example 1, except that less catalyst complex was employed, isopropylbenzene was produced. In this example, the aluminum chloride catalyst comprised 0.076 weight percent based on the weight of the diisopropylbenzene-benzene reaction mixture. After 60 minutes of reaction, gas chromatographic analysis showed a diisopropylbenzene transalkylation of 60 percent. Thus, even though the catalyst concentration was 28 percent less than in Example 1, the conversion to desired product was 27 percent greater than was obtained in the comparative run shown in Example 1.

EXAMPLE 3

In a manner similar to that described in Example 1, except that the catalyst complex was added in an amount to give an aluminum chloride concentration of 0.1 weight percent and the amount of hydrogen chloride added during the reaction was only a tenth of the amount used in Example 1, i.e. over 60 minutes 1.5 molar equivalents per mole of aluminum chloride were added to the reaction mixture, isopropylbenzene was produced. After 60 minutes of reaction gas chromatographic analysis showed a diisopropylbenzene transalkylation of 77 percent. The process was repeated except that the amount of hydrogen chloride added was further reduced, this time to a mole ratio with aluminum chloride of from 0.7-1:1. After 60 minutes of reaction the diisopropylbenzene transalkylation was 72 percent.

For comparative purpose the foregoing procedure was repeated except that the improvement of this invention was not employed, i.e. there was no hydrogen chloride added to the reaction mixture during the reaction. After 60 minutes of reaction diisopropylbenzene transalkylation was only 49 percent.

The results demonstrate that addition during the reaction only 1.5 moles of hydrogen chloride per mole of aluminum chloride increased the catalyst activity by 57 percent and addition during the reaction of only 0.7-1 mole of hydrogen chloride per mole of aluminum chloride increases the catalyst activity by 47 percent over that observed in the comparative experiment when the improved process of this invention was not employed.

EXAMPLE 4

In this example the procedure was similar to that described in Example 3 except that the catalyst complex was added in an amount to give an aluminum chloride concentration of 0.095 weight percent and 0.32 molar equivalents of hydrogen chloride per mole of aluminum chloride were added to the reaction mixture over the reaction time. After 60 minutes of reaction, gas chromatographic analysis showed a diisopropylbenzene transalkylation of 69 percent. The process was repeated except that the amount of hydrogen chloride added during the reaction was reduced still further, this time only 0.13 molar equivalents per mole of aluminum chloride were added. After 60 minutes of reaction the diisopropylbenzene transalkylation was 66 percent.

For comparative purposes the foregoing procedure was repeated except that there was no hydrogen chloride added to the reaction mixture during the reaction. After 60 minutes of reaction the diisopropylbenzene conversion was only 48 percent.

The results demonstrates that the addition during the reaction only 0.32 mole of hydrogen chloride per mole of aluminum chloride increased the catalyst activity by 44 percent and addition during the reaction of only 0.13 mole of hydrogen chloride per mole of aluminum chloride increased the catalyst activity by over 37 percent.

EXAMPLE 5

There was charged to a 1000 ml 3-neck reaction flask equipped with a septum, gas inlet tube, magnetic stirring bar and Claisen adapter with thermometer and condenser which was connected to a glass tube immersed in mercury such that the pressure of the system was set by the height of the mercury, a mixture of 32 grams of diisopropyl benzene in 456 grams of benzene. The mixture was dehydrated by azeotropic distillation of 100 ml (88 grams) benzene and water and the reaction flask was then purged and pressurized with nitrogen to 1.25 atmospheres. Then hydrogen chloride was continuously added throughout the reaction. Constant pressure at 1.25 atmospheres was maintained by venting the excess gas through a mercury pressure regulator.

A catalyst complex was prepared as in Example 1 and was added to the reaction flask in an amount such that the aluminum chloride was 0.1 weight percent based on the weight of the diisopropylbenzene-benzene mixture. The temperature of the reaction mixture was raised to reflux, approximately 90° C., and hydrogen chloride was added in such a manner that in 60 minutes 18 molar equivalents per mole of aluminum chloride were added to the reaction mixture. After 60 minutes, gas chromatographic analysis showed a diisopropylbenzene transalkylation to desired isopropylbenzene of 91 percent.

For comparative purposes the above-described procedure was repeated except that the gaseous hydrogen chloride was not added during the reaction; thus the pressure of the reaction was maintained solely through the use of nitrogen. After 60 minutes, the transalkylation was only 69 percent.

The results demonstrate that the improved process of this invention is useful at superatmospheric pressures. In this instance, the improvement observed was a 46 percent increase in transalkylation.

EXAMPLE 6

In this example, the procedure was similar to that of Example 5 except that less catalyst complex was employed; the aluminum chloride catalyst was 0.073 weight percent based on the weight of the reaction mixture. After 60 minutes of reaction, gas chromatographic analysis showed a diisopropylbenzene transalkylation of 84 percent. Thus, even though the catalyst concentration was reduced by 27 percent, the conversion to desired product was about 22 percent greater than was obtained in the comparative run shown in Example 5.

EXAMPLE 7

Using the apparatus and procedure described in Example 5, but maintaining a pressure of 1.5 atmospheres and a temperature at reflux of about 95° C., two runs were carried out. In the first run the aluminum chloride concentration was 0.074 weight percent and the hydrogen chloride addition was 18 molar equivalents per mole of aluminum chloride and in the second run the aluminum chloride concentration was 0.061 weight percent and the hydrogen chloride addition was 22 molar equivalents per mole of aluminum chloride; the diisopropylbenzene transalkylation after 60 minutes of reaction was 92 percent and 84 percent, respectfully.

For comparative purposes the above procedure was repeated except that the aluminum chloride concentration was 0.101 weight percent and there was no addition of hydrogen chloride during the reaction; the pressure of the reaction was maintained solely through the use of nitrogen. After 60 minutes the conversion was only 81 percent.

Thus, even though the catalyst concentration was reduced by 27 percent in the first run and by nearly 40 percent in the second run over the amount used in the comparative run, in each of these two runs the transalkylation exceeded that of the comparative run; by 16 percent in the first run and by 4 percent in the second run.

EXAMPLE 8

The reaction and procedure of Example 5 were repeated except that the reaction temperature was below reflux; in this case it was 82° C. The diisopropylbenzene transalkylation after 60 minutes was 91 percent.

For comparative purposes the procedure described above was repeated except that there was no hydrogen chloride addition; the reaction pressure was maintained solely through the use of nitrogen. After 60 minutes the conversion was only 77 percent.

The results show that the improved process of this invention is useful at temperatures below reflux; in this case resulting in an increase in catalyst activity of 18 percent.

What is claimed is:

1. In the Friedel-Crafts alkylation or transalkylation reactions for the production of alkaryl compounds by the catalytic reaction of aromatic compounds with an alkyl halide having from 1 to 20 carbon atoms, alkene having from 2 to 20 carbon atoms or alkyne having from 2 to 20 carbon atoms in contact with the Friedel-Crafts catalyst comprising a metal halide and a hydrogen halide or alkyl halide having from 1 to 20 carbon atoms, the improvement of adding gaseous hydrogen halide to the liquid reaction mixture during at least a part of such reaction, said gaseous hydrogen halide being added at a mole ratio of gaseous hydrogen halide to said metal halide of at least 0.01:1.

2. The process as claimed in claim 1, wherein said gaseous hydrogen halide is introduced in a concentration of from 0.01 to 20 moles per mole of said metal halide.

3. The process as claimed in claim 1, wherein said gaseous hydrogen halide is introduced in a concentration of from 0.1 to 1 mole of said metal halide.

4. The process as claimed in claim 1, wherein said gaseous hydrogen halide is hydrogen chloride.

5. The process as claimed in claim 1, wherein in said catalyst said metal halide is aluminum chloride and said alkyl halide is isopropyl chloride.

6. The process as claimed in claim 1, wherein said aromatic compounds are a mixture of diisopropylbenzene and benzene.

7. The process as claimed in claim 1, wherein said catalyst is present in a concentration such that the metal halide content in the reaction mixture is from about 0.01 weight percent to about 5 weight percent based on the weight of aromatic compounds present in the reaction mixture.

8. A process as claimed in claim 1, wherein said catalyst is present in a concentration such that the metal halide content in the reaction mixture is from about 0.01 to about 1 weight percent based on the weight of aromatic compounds present in the reaction mixture.

9. A process as claimed in claim 1, wherein said catalyst is present in a concentration such that the metal halide content in the reaction mixture is from about 0.05 to about 0.15 weight percent based on the weight of aromatic compounds present in the reaction mixture.

10. The process as claimed in claim 1, wherein said gaseous hydrogen halide is added to the liquid reaction mixture throughout the entire reaction period.

11. A process as claimed in claim 1, wherein the gaseous hydrogen halide is added to the reaction mixture at a constant rate.

* * * * *